(12) United States Patent
Parker

(10) Patent No.: US 7,230,063 B1
(45) Date of Patent: Jun. 12, 2007

(54) FUNCTIONAL TRITHIOCARBONATE RAFT AGENTS

(75) Inventor: Dane Kenton Parker, Coshocton, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 11/583,624

(22) Filed: Oct. 19, 2006

Related U.S. Application Data

(60) Provisional application No. 60/753,145, filed on Dec. 22, 2005.

(51) Int. Cl.
*C08F 12/08* (2006.01)
*C08F 2/38* (2006.01)
*C07C 381/00* (2006.01)

(52) U.S. Cl. ............... 526/346; 526/204; 526/211; 526/214; 526/222; 526/303.1; 526/328; 526/340; 526/341; 526/343; 526/344; 558/243; 562/426; 562/581

(58) Field of Classification Search ............... 562/426, 562/512, 581; 568/75; 526/204, 211, 214, 526/222, 340, 346, 303.1, 328, 343, 344; 558/243
See application file for complete search history.

(56) References Cited

U.S. PATENT DOCUMENTS 4,868,322 A * 9/1989 Degani et al. ............ 558/243

| | | | |
|---|---|---|---|
| 6,596,899 B1 * | 7/2003 | Lai | 562/426 |
| 6,998,452 B1 * | 2/2006 | Parker | 526/194 |
| 2005/0009999 A1 * | 1/2005 | Lai et al. | 525/461 |

OTHER PUBLICATIONS

Liu, et al, Dihydroxyl-terminated telechelic polymers prepared by RAFT polymerization using functional trithiocarbonate as chain transfer agent, Polymer 45 (2004) 4413-4421.*
You, et al, Preparation and Characterization of Thermally Responsive and Biodegradable Block Copolymer Comprised of PNIPAAM and PLA by Combination of ROP and RAFT Methods, Macromolecules 2004, 37, 9761-9767.*

* cited by examiner

*Primary Examiner*—Fred Teskin
(74) *Attorney, Agent, or Firm*—John D. DeLong

(57) ABSTRACT

The present invention is directed to a free radical control agent of the structural formula:

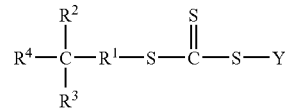

wherein $R^1$ is a divalent alkyl group of 1 to 12 carbon atoms, $R^2$ and $R^3$ are each independently hydrogen or an alkyl group of 1 to 12 carbon atoms, and $R^4$ is —OH or —COOH, with the proviso that the total carbon atoms of $R^1$, $R^2$, and $R^3$ is no greater than 12; and wherein Y represents a functional group that is capable of activating a vinylic carbon toward free radical addition.

10 Claims, No Drawings

FUNCTIONAL TRITHIOCARBONATE RAFT AGENTS

CROSS REFERENCE TO OTHER APPLICATIONS

This application claims the benefit of Ser. No. 60/753,145 filed Dec. 22, 2005.

BACKGROUND OF THE INVENTION

"RAFT" is an acronym that stands for reversible addition-fragmentation chain transfer. It is but one of several controlled free radical polymerization (CFRP) systems in general use. RAFT is a robust and versatile system and amenable to emulsion polymerization. The RAFT process is mediated by RAFT agents. These agents are typically derived from specific dithioesters, xanthates, dithiocarbamates and trithiocarbonates designed to have both high chain transfer constants and good radical polymerization reinitiating efficiency.

With the current state of RAFT-CFRP technology, polymers of low polydispersity (PDI) and complex architecture can be synthesized in bulk or solution with relative ease. The major obstacle that remains to their widespread commercial use has been the difficulty in adapting CFRP methods to polymerization in aqueous dispersion (emulsion). Polymerization in waterborne organic dispersions is an environmentally superior way to conduct radical polymerizations because the need for organic solvents is eliminated.

The degenerative RAFT mechanism does not drastically affect the radical concentration in the particle which in turn, leads to a similar kinetic behavior seen in typical emulsion polymerization. Unfortunately, the use RAFT agents in typical ab initio (unseeded) emulsion polymerization have not proven to be straightforward. Problems include severe retardation, loss of molecular weight control, loss of colloidal stability and/or the formation of highly colored oily layers. Various reasons for this behavior are possible, such as the formation of destabilizing oily oligomers, and poor transport of RAFT agent from the monomer droplets through the water phase to the loci of polymerization in the micelles.

To overcome these problems and achieve successful emulsion polymerization under RAFT control, several techniques have been developed. One method uses the combination of preformed seed latex, a highly hydrophobic RAFT agent and acetone as an additive to aid in the transport of the RAFT agent through the water phase and into the seed particle. Subsequent swelling of the seed particles with monomer in the presence of a water soluble initiator lead to a controlled free radical polymerization. Another method uses an amphipathic RAFT agent which can mediate polymerization in both the aqueous and organic phases. RAFT in miniemulsion systems has also been tried with mixed results. While many of these techniques have been shown to work, most lack generality or suffer practical difficulties for commercial application.

SUMMARY OF THE INVENTION

The present invention is directed to a free radical control agent of the structural formula:

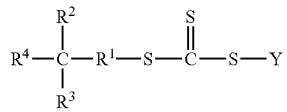

wherein R1 is a divalent alkyl group of 1 to 12 carbon atoms, $R^2$ and $R^3$ are each independently hydrogen or an alkyl group of 1 to 12 carbon atoms, and $R^4$ is —OH or —COOH, with the proviso that the total carbon atoms of $R^1$, $R^2$, and $R^3$ is no greater than 12; and wherein Y represents a functional group that is capable of activating a vinylic carbon toward free radical addition.

DESCRIPTION OF THE INVENTION

The RAFT process functions by a degenerative mechanism as shown in the following equation 1.

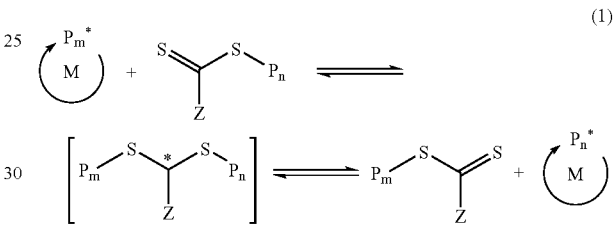

(1)

Among the specific types of RAFT agents that can be synthesized, the trithiocarbonate class stands out as being readily synthesized and highly active. Symmetrical and unsymmetrical trithiocarbonates can be prepared by nucleophilic displacement reactions (see Eqs. 2 and 3).

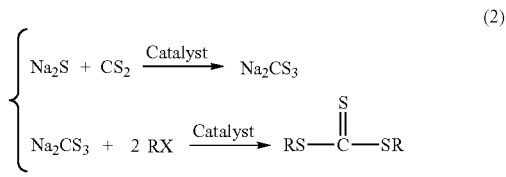

(2)

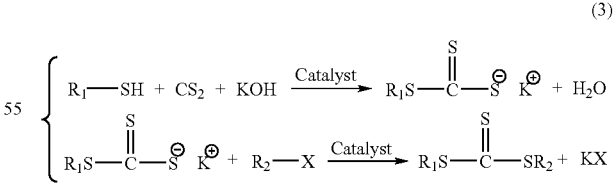

(3)

Only specific types of "R" groups are active enough by the mechanism shown in Eq. 1 to cleave from the original RAFT agent (a trithiocarbonate in this case) and reinitiate polymerization. Commonly such groups provide benzylic or stabilized tertiary alkyl radical species. Therefore, in the case of Eq.2 where both "R" groups are benzyl, we have a difunctional RAFT agent (DBTTC) capable of growing in two directions at once to yield a controlled molecular weight polystyrene with a trithiocarbonate group in the center of the molecule and benzyl groups

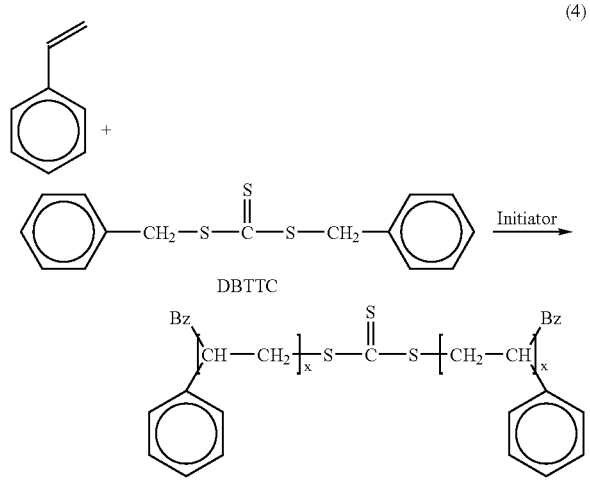

(4)

If, on the other hand, as in Eq. 3 both "R" groups are not identical but one is capable of radical reinitiation (e.g., a benzyl group) then a situation arises where the polymer chain will grow in a controlled manner from only one end (see Eq. 5).

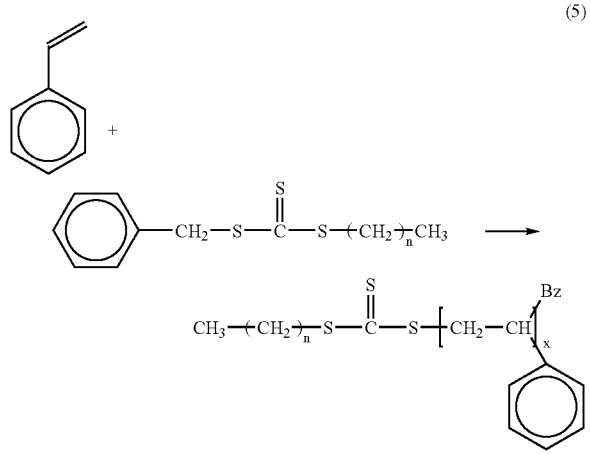

(5)

In Eq. 5, the linear alkyl group is not active in the polymerization and only the benzyl group propagates the radical polymerization.

Development of a successful and practical RAFT-based controlled free radical emulsion polymerization process depends upon finding the solution to several problems. First, finding a simple emulsification method that would mimic a miniemulsion system, that is, a system wherein the primary locus of polymerization is within microemulsified monomer droplets and not soap micelles. This type of system will eliminate the requirement that the RAFT agent be able to migrate through the water phase from monomer droplets to the micelles. All the microemulsified monomer droplets will then contain the same fixed ratio of monomer to RAFT agent. The second issue revolves around finding a readily prepared RAFT agent having high activity, good solubility in the monomers and preferably slight solubility in the aqueous phase.

A solution to the first problem has now been found in the so-called "In-Situ" emulsification method. "In-Situ" emulsification may be defined in terms of a process modification of "classical" emulsion polymerization, where a latent surfactant precursor such as oleic acid is dissolved in monomer prior to adding an aqueous solution containing a base (e.g., potassium hydroxide). As the two-phase system is mixed, surfactant (potassium oleate) is generated and an emulsion forms. This is in contrast to the more prevalent industrial mode of emulsification, where a preformed surfactant solution is mixed with monomer at about 600 to 800 rpm until a uniform emulsion is prepared. However, this seemingly minor process modification has profound implications for emulsion polymerization, in general, and for the practical implementation of controlled free radical emulsion polymerization, in particular. Linking the "in-situ" emulsification technique to the RAFT-CFRP mechanism has now been found to be a key component to a practical process.

The solution to the second problem would appear to reside in selecting the proper RAFT agent to provide the desired solubility characteristics in an emulsified system. Trithiocarbonates may be readily prepared following the procedures described herein. At least one of the "R" groups on the trithiocarbonate should be benzylic or tertiary alkyl group to provide radicals that will reinitiate polymerization. As previously mentioned, unsymmetrical trithiocarbonates can contain two different "R" groups. Therefore, to add a small degree of hydrophilic character a polar group could be introduced onto one or both "R" groups.

One technique to prepare such a mildly hydrophilic unsymmetrical trithiocarbonate would be to use a functional thiol to first prepare an alkali metal trithiocarbonate salt followed by alkylation with a benzylic halide. One method to prepare a functional thiol such as a β-hydroxythiol, is to react an epoxide with hydrogen sulfide. The overall process for the formation of the unsymmetrical trithiocarbonate is shown in the following Eqs.

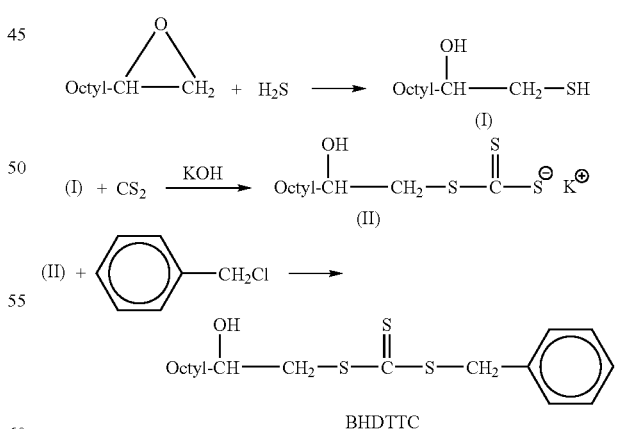

BHDTTC=S-Benzyl-S'-(2-hydroxydecyl)trithiocarbonate

The key ingredient in this synthetic scheme, β-hydroxydecanethiol (HDT), can be readily prepared in high yield by the catalyzed reaction of epoxides with hydrogen sulfide according to the teachings found in U.S. Pat. No. 4,985,586.

More generally, the free radical control agent is of the structural formula:

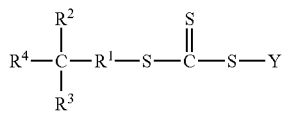

wherein $R^1$ is a divalent alkyl group of 1 to 12 carbon atoms, $R^2$ and $R^3$ are each independently hydrogen or an alkyl group of 1 to 12 carbon atoms, and $R^4$ is —OH or —COOH, with the proviso that the total carbon atoms of $R^1$, $R^2$, and $R^3$ is no greater than 12; and wherein Y represents a functional group that is capable of activating a vinylic carbon toward free radical addition.

In one embodiment, Y represents a functional group selected from the group consisting of —C(R')$_2$CN, —C(CH$_3$)$_2$Ar, —C(CH$_3$)$_2$COOR', —C(CH$_3$)$_2$CONHR', —C(CH$_3$)$_2$CH$_2$C(CH$_3$), —CH(CH$_3$)Ar, —CH$_2$Ar, —C(CH$_3$)$_3$, —CR$_{12}$COOH, —C(R')(CN)—(CH$_2$)$_n$—COOH, and —C(R')(CN)—(CH$_2$)$_n$—OH; wherein R' represents a linear or branched hydrocarbon containing from 1 to 12 carbon atoms; wherein Ar represents an unsubstituted or substituted phenyl, napthyl, anthracenyl, pyrenyl or pyridyl group; and wherein n represents an integer from 1 to 8.

In another embodiment, Y represents a function group selected from the group consisting of benzyl, picolyl, or t-butyl.

In another embodiment, $R^1$ is a divalent alkyl group of 1 to 4 carbon atoms, i.e., $R^1$ is (CH$_2$)$_m$ where m ranges from 1 to 4.

In another embodiment, $R^1$ is (CH$_2$)$_9$, $R^2$ and $R^3$ are hydrogen, $R^4$ is —COOH, Y is benzyl, and the free radical control agent is S-benzyl-S'-(11-undecanoic acid)trithiocarbonate.

In another embodiment, $R^1$ is CH$_2$, $R^2$ is (CH$_2$)$_8$, $R^3$ is hydrogen, $R^4$ is —OH, Y is benzyl, and the free radical control agent is S-benzyl-S'-(2-hydroxydecyl)trithiocarbonate.

In another embodiment, $R^1$ is CH$_2$, $R^2$ is (CH$_2$)$_8$, $R^3$ is hydrogen, $R^4$ is —OH, Y is 4-picolyl, and the free radical control agent is S-(4-picolyl)-S'-(2-hydroxydecyl)trithiocarbonate.

The unsymmetrical trithiocarbonate free radical control agents of the present invention can be used in conducting controlled polymerizations. Such polymers are particularly useful in manufacturing polymeric compositions such as tire tread compounds. In any case, such controlled polymerizations are conducted in the presence of the free radical control agents made by the synthesis process of this invention.

The controlled polymerization can be a batch, semi-batch, or continuous process which provides excellent control of the polymer composition and morphology. The controlled polymerization will normally be carried out as an emulsion polymerization process.

Monomers that may be polymerized in a controlled polymerization using the free radical control agents of this invention include at least one monomer selected from the group consisting of styrene, substituted styrene, alkyl acrylate, substituted alkyl acrylate, alkyl methacrylate, substituted alkyl methacrylate, acrylonitrile, methacrylonitrile, acrylamide, methacrylamide, N,N-dialkylacrylamide, N,N-dialkylmethacrylamide, isoprene, 1,3-butadiene, ethylene, vinyl acetate, vinyl chloride, vinylidene chloride, and combinations thereof. Functionalized versions of these monomers may also be used. Specific monomers or co-monomers that may be used in this invention and from which M is derivable include methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, α-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolmethacrylamide, N-ethylolmethacrylamide, N-tert-butylacrylamide, N-n-butylacrylamide, N-methylolacrylamide, N-ethylolacrylamide, vinyl benzoic acid (all isomers), diethylaminostyrene (all isomers), α-methylvinyl benzoic acid (all isomers), diethylamino alpha-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, maleic anhydride, N-phenylmaleimide, N-butylmaleimide, chloroprene, ethylene, vinyl acetate, vinyl chloride, vinylidene chloride, 2-(2-oxo-1-imidazolidinyl) ethyl 2-methyl-2-propenoate, 1-[2-[2-hydroxy-3-(2-propyl) propyl]amino]ethyl]-2-imidazolidinone, N-vinyl pyrrolidone, N-vinyl imidazole, crotonic acid, vinyl sulfonic acid, and combinations thereof. In one embodiment, the monomer is selected from 1,3-butadiene, styrene, and isoprene.

Controlled polymerization requires the presence of a free radical control agent to control the course of polymerization while minimizing undesirable side reactions, such as chain termination. The control agent has characteristics that depend greatly on the details of the polymerization, including the mechanism for polymerization, the types of monomers being used, the type of initiation, the solvent system and the reaction conditions. In one embodiment, the control agent may be a control agent for polymerization by a free radical mechanism, such as reversible-addition fragmentation transfer (RAFT). The control agent may be introduced into the emulsion system by many different methods, and the preferred method depends greatly on the particular embodiment being practiced. In some embodiments, the active control agent may be added directly to the reaction vessel in the form of a pure compound or as a component of a solution or mixture. In other embodiments, the active control agent may be generated in situ from chemical reactions occurring prior to, during or after emulsification.

Regardless of the method used to introduce or generate a control agent, the control agents suitable for the present invention offer one or more of the benefits associated with "living" polymerization kinetics. These benefits may include: (1) a linear dependence of the degree of polymerization as a function of time; (2) a linear dependence of the number-average molecular weight (Mn) on the extent of polymerization; (3) a constant number of polymer molecules and active centers that is sensibly independent of conversion; (4) a narrow molecular weight distribution, with Mw/Mn generally less than 2, preferably between 1.1 and 1.8, and often below 1.4; and (5) essentially complete conversion of monomer to polymer with the ability to continue polymerization upon addition of more monomer.

All polymerization reactions must be initiated. For some monomers, such as styrene for example, thermal self-initiation can occur without the need for additional reagents. For many other monomers, initiation may be accomplished by adding an agent to trigger one or more chemical reactions that ultimately produces an intermediate capable of propagating polymerization. These agents often are referred to as "initiators."

The type of initiators suitable for the present invention depend greatly on the details of the polymerization, including the mechanism for polymerization, the types of monomers being used, the type of control agent, the solvent system and the reaction conditions. Many different types of initiators have been investigated.

The initiator may be an initiator for polymerization by a free radical mechanism, such as RAFT or a related mechanism involving stable free radicals. Typically, suitable initiators for free radical polymerization are reagents or combinations of reagents that are capable of producing free radicals. Other methods for producing free radicals, including exposure to ionizing radiation ($^{60}$Co γ-rays), photochemical reactions, or sonication, will be evident to those of skill in the art as suitable methods for initiating free radical polymerization.

Some representative examples of free radical initiators which are commonly used include the various peroxygen compounds such as potassium persulfate, ammonium persulfate, benzoyl peroxide, hydrogen peroxide, di-t-butyl peroxide, dicumyl peroxide, 2,4-dichlorobenzoyl peroxide, decanoyl peroxide, lauryl peroxide, cumene hydroperoxide, p-menthane hydroperoxide, t-butyl hydroperoxide, acetyl acetone peroxide, dicetyl peroxydicarbonate, t-butyl peroxyacetate, t-butyl peroxymaleic acid, t-butyl peroxybenzoate, acetyl cyclohexyl sulfonyl peroxide, and the like; the various azo compounds such as 2-t-butylazo-2-cyanopropane, dimethyl azodiisobutyrate, azodiisobutyronitrile, 2-t-butylazo-1-cyanocyclohexane, 1-t-amylazo-1-cyanocyclohexane, and the like; the various alkyl perketals, such as 2,2-bis-(t-butylperoxy)butane, ethyl 3,3-bis(t-butylperoxy) butyrate, 1,1-di-(t-butylperoxy)cyclohexane, and the like. Persulfate initiators, such as potassium persulfate and ammonium persulfate, are especially useful in such aqueous emulsion polymerizations.

Polymerization can also be initiated with free radicals that are generated utilizing redox initiators, such as combinations of chelated iron salts, sodium formaldehyde sulfoxylate, and organic hydroperoxides. Some representative examples of such organic hydroperoxides include cumene hydroperoxide, paramenthane hydroperoxide, and tertiary butyl hydroperoxide. Tertiary butyl hydroperoxide (t-BHP), tertiary butyl peracetate (t-BPA) and "azo" initiators, such as azobisiobutyronitrile (AIBN), are preferred for use in generating free radicals.

In batch operations, the polymerization time can be varied as desired; it may vary, for example, from a few minutes to several days. Polymerization in batch processes may be terminated when monomer is no longer absorbed, or earlier, if desired, e.g., if the reaction mixture becomes too viscous. In continuous operations, the polymerization mixture may be passed through a reactor system of any suitable design. The polymerization reactions in such cases are suitably adjusted by varying the residence time. Residence times vary with the type of reactor system and the size of the reactors, for example, from 10 to 15 minutes to 24 or more hours.

Surfactants are essential in the case of controlled emulsion polymerizations, and suitable surfactants include any compound or mixture of compounds capable of stabilizing colloidal aqueous emulsions. Generally, surfactants are amphiphilic molecules that reduce the surface tension of liquids, or reduce interfacial tension between two liquids or a liquid and a solid. Surfactants may be small molecules or polymers, micelle-forming or non-micelle-forming, and may be anionic, cationic, zwitterionic or nonionic. In some embodiments of the present invention, mixtures of surfactants are used. The amount of surfactant used typically ranges from about 0.01 to about 200 percent by weight relative to the monomer, with a more preferred range being from about 0.1 to about 8 percent by weight and a more specifically preferred range being from about 0.5 to about 3 percent by weight. Those skilled in the art typically consider a number of factors when selecting surfactants for a particular application, including economic factors (see *Detergents Handbook*, McCutcheon Division, Manufacturing Confectioner Publishing Co, Glen Rock, N.J., 1999). Suitable anionic surfactants include substituted or unsubstituted hydrocarbyl sulfates, sulfonates, carboxylates, phosphonates and phosphates having between 6 and 30 carbon atoms per anionic functional group. Suitable cationic surfactants include substituted or unsubstituted hydrocarbyl ammonium salts having between 6 and 30 carbon atoms per cationic functional group. Suitable nonionic surfactants include amphiphilic amides having between 6 and 30 carbon atoms for each hydrocarboyl group and between 2 and 30 carbon atoms for each hydrocarbyl amine group. A broad range of suitable surfactants is described in *McCutcheon's Emulsifiers*. For each surfactant, one or more hydrogen or carbon atom from the hydrocarbyl groups may have replaced with another atom selected from the group consisting of N, S, O, Si, F, Cl, Br and I. The hydrocarbyl may also have one or more hydrogen or carbon atom replaced with a functionality such as a keto, ester, amide, ether, thioether, hydroxyl and the like, and the hydrocarbyl may be part of a ring structure.

In some embodiments, useful surfactants include, for example, alkali metal and ammonium salts of:
 (i) alkylsulfates (alkyl radical: $C_8$ to $C_{18}$);
 (ii) alkylarylsulfonic acids (alkyl radical: $C_9$ to $C_{18}$);
 (iii) alkanesulfonic acids (alkyl radical: $C_8$ to $C_{18}$);
 (iv) succinate half-amides of alkylamines (alkyl radical: $C_8$ to $C_{18}$);
 (v) succinate half-esters of alkanols (alkyl radical: $C_8$ to $C_{18}$);
 (vi) alkanoic acids (alkyl radical: $C_8$ to $C_{18}$);
 (vii) alkylphosphates (alkyl radical: $C_1$ to $C_{18}$);
 (viii) alkylphosphonates (alkyl radical: $C_1$ to $C_{18}$);
 (ix) acylated sarcosine and taurine (acyl radical $C_8$ to $C_{18}$); and (x) sulfosuccinic acid diesters and diamides (alkyl radical: $C_4$ to $C_{18}$).

In other embodiments, useful surfactant include, for example:
(i) alkanol amides (alkyl radical: $C_2$ to $C_{18}$);
(ii) quaternized amines (alkyl radical: $C_1$ to $C_{18}$), including amine oxide derivatives;
(iii) quaternized nitrogen-containing heterocycles with pendant alkyls (alkyl radical: $C_4$ to $C_{18}$);
(iv) betaine derivatives (alkyl radical: $C_8$ to $C_{18}$); and
(v) amphiphilic block copolymers.

An important aspect of the present invention is in-situ emulsification, which is achieved by reacting a "latent surfactant" with a "surfactant activator" to produce the surfactant for controlled emulsion polymerization. As used herein, the term "latent surfactant" refers to a compound or mixture of compounds that: (i) is soluble in a monomer-containing solution that is not miscible with water; and (ii) is not independently capable of producing a stabilized colloidal microemulsion at conventional surfactant levels from simple gentle mixing of the compound or mixture of compounds with monomer-containing solution and water. The term "surfactant activator" is used herein to describe a compound or mixture of compounds that: (i) is soluble in water; and (ii) is not independently capable of producing a stabilized colloidal microemulsion at conventional surfactant levels from simple gentle mixing of the compound or mixture of compounds with monomer-containing solution and water. For the present invention, water can be a reactant for in-situ emulsification reactions, but water alone cannot be the surfactant activator. The use of an in-situ emulsification technique in a controlled polymerization process that can be used in accordance with this invention is described in U.S. patent application Ser. No. 10/721,718, filed on Nov. 25, 2003, now U.S. Pat. No. 6,992,156. The teachings of U.S. patent application Ser. No. 10/721,718 are incorporated herein by reference in their entirety.

The fundamental principles for in-situ microemulsification are described by Prokopov and Gritskova (*Russ. Chem. Rev* 2001, 70, 791), who review its use in conventional free-radical polymerization of styrene using alkali-metal soaps prepared in situ via neutralization of fatty acids. As explained by Prokopov and Gritskova, the preparation of a carboxylate soap at a styrene-water interface during emulsification can produce a fine microemulsion because interfacial tension is decreased significantly by an abundance of emulsifier produced at the interface. By varying the nature of the carboxylic acid and the metal counter-ion used in the surfactant synthesis at the interface, it was possible to control the degree of dispersion and stability of the emulsion, as well as the resulting polystyrene latex produced via conventional free radical polymerization. In the present invention, the principles of in-situ microemulsification are expanded broadly to produce emulsions suitable for controlled polymerization via a wide range of methods utilizing conventional soap levels without added hydrophobes or specialized emulsification equipment.

In some embodiments, the surfactant for controlled polymerization may be produced by an acid/base neutralization reaction at the monomer/water interface. For some types of anionic surfactants, this may be accomplished, for example, via reaction of a monomer-soluble acid with an aqueous base, where the monomer-soluble acid is the latent surfactant and the base is the surfactant activator for in-situ emulsification. Suitable monomer-soluble acids include, for example, palmitic acid, oleic acid, dodecylbenzene sulfonic acid, lauryl sulfate, hexadecylsulfonic acid, dihexadecylphosphonic acid, hexadecylsuccinate half ester, and the monohexadecylamide of succinic acid. Suitable bases include, for example, hydroxides, carbonates and bicarbonates of alkali metal ions and quaternary ammonium ions, substituted and unsubstituted amines, and basic nitrogen-containing heterocycles. It will be evident to those skilled in the art that any aqueous base with a pKb less than about the pKa of the monomer-soluble acid also may be suitable. It also will be evident that hydroxides generated in situ via hydrolysis of moisture-sensitive compounds, such as sodium methoxide, sodium amide, potassium hydride and the like, also may be suitable as surfactant activators.

For some types of cationic surfactants, in situ synthesis during emulsification may be accomplished, for example, via reaction of a monomer-soluble base with an aqueous acid, where the monomer-soluble base is the latent surfactant and the acid is the surfactant activator. Suitable monomer-soluble bases include, for example, hexadecyldimethylamine, hexadecyldimethylamine oxide, and amphiphilic nitrogen-containing heterocycles. Suitable acids include for example mineral acids, sulfonic acids and phosphonic acids. It will be evident to those skilled in the art that any aqueous acid with a pKa less than about the pKb of the monomer-soluble base also may be suitable. It also will be evident that acids generated in situ via: hydrolysis of moisture-sensitive compounds, such as Lewis acids, acyl halides, acyl anhydrides, mineral acid anhydrides, hydrolyzable transition-metal halides, main group halides and the like, also may be suitable as surfactant activators.

In some embodiments, surfactant may be produced in situ by chemical reactions that attach hydrophilic functionality to a functionalized hydrophobe. For these embodiments, the functionalized hydrophobe is the latent surfactant and the reagent or reagents necessary for attaching the hydrophilic functionality serve as surfactant activator. For some types of surfactants this may be accomplished, for example, via reaction of a monomer-soluble electrophile with an aqueous nucleophile. Suitable electrophiles include for example:
(i) hydrocarboyl halides;
(ii) hydrocarboyl esters;
(iii) hydrocarboyl anhydrides;
(iv) hydrocarbyl isocyanates;
(v) hydrocarbyl halides; and
(vi) hydrocarbyl esters of sulfonic acids.

Suitable surfactant activators include for example:
(i) amine-functionalized hydrocarbylsulfates, hydrocarbylcarboxylates, hydrocarbylphosphates, hydrocarbylammonium salts;
(ii) diethanol amine;
(iii) diethylenetriamine and other aminoamines;
(iv) amino-polyethyleneglycols and polyethyleneglycol ethers;
(v) aminoglycosides;
(vi) aminobetaines;
(vii) hydroxides of alkali metal ions and quaternary ammonium ions; and
(viii) hydrocarbylamines.

For some types of surfactants, in-situ synthesis and emulsification may be accomplished by reaction of a monomer-soluble nucleophile with an aqueous electrophile. Suitable nucleophiles include for example, hexadecylamine and hexadecyldimethylamine. Suitable electrophiles include for example succinic anhydride, dimethylsulfate and 1,3-propanesultone.

Many other reactions can be used to synthesize surfactants in situ, and the specific embodiments illustrated above are not intended to preclude any combination of latent surfactant/surfactant activator that produces a surfactant during emulsification. It will be evident to those skilled in the art that other latent surfactant/surfactant activator combinations may be suitable when the chemistries of surfactant synthesis and controlled polymerization are compatible.

Polymers produced using the RAFT agents of the invention may be used in rubber compositions in tire components. Such components may include but are not limited to treads, sidewalls, sidewall inserts, plycoats, apexs, chafers, wire coats, and the like. It is readily understood by those having skill in the art that rubber compositions used in tire components would be compounded by methods generally known in the rubber compounding art, such as mixing the various sulfur-vulcanizable constituent rubbers with various commonly used additive materials such as, for example, curing aids, such as sulfur, activators, retarders and accelerators, processing additives, such as oils, resins including tackifying resins, silicas, and plasticizers, fillers, pigments, fatty acid, zinc oxide, waxes, antioxidants and antiozonants, peptizing agents and reinforcing materials such as, for example, carbon black and silica. As known to those skilled in the art, depending on the intended use of the sulfur vulcanizable and sulfur vulcanized material (rubbers), the additives mentioned above are selected and commonly used in conventional amounts. The components and tire can be built, shaped, molded and cured by various methods which will be readily apparent to those having skill in such art.

The practice of this invention is further illustrated by the following examples which are intended to be representative rather than restrictive of the scope of the subject invention. Unless indicated otherwise, all parts and percentages are given by weight.

EXAMPLE 1

Synthesis of
S-Benzyl-S'-(2-hydroxydecyl)trithiocarbonate (BHDTTC)

A one liter three neck round bottomed flask equipped with a mechanical paddle stirrer, nitrogen inlet, pot thermometer and condenser, was charged under a slow nitrogen bleed with 95 g (~0.50 moles) of β-hydroxydecanethiol (HDT). To the stirred HDT, was then added an aqueous solution of 32.0 g of 87.6 percent pure KOH (~0.50 moles) dissolved in 248 g of water. After stirring for 15 min. at ambient temperature, a solution of 78 g (~1.0 mole) of carbon disulfide and 1.0 g of Aliquat 336 were added to the mixture. The solution rapidly turns yellow and a small amount of solid precipitated from solution. The solution temperature increased to about 44° C. and was controlled using slight cooling from a water bath. After 15 min., 60.1 g (0.0475 moles) of benzyl chloride were added. Again the temperature was maintained at about 44° C. until the exotherm subsided. At this point, the mixture was heated for one hour at 50° C. Let stand at room temperature overnight then add 50 ml of dichloromethane. Separate off the lower product phase and strip off solvent at reduced pressure to obtain 184.3 g of crude product; ~94 percent crude yield as a yellow oil that crystallizes rapidly. Verification of the main component in the crude reaction mixture as being BHDTTC was obtained using electro-spray ionization mass spectrometry (ESI-MS). The crude product was used for subsequent emulsion polymerization studies.

EXAMPLE 2

Synthesis of S-Benzyl-S'-dodecyl trithiocarbonate (BDTTC)

Procedure is identical to that of Ex. 1 except that 1-dodecanethiol was substituted for HDT. Crude product crystallizes into a bright yellow solid within a few hours at room temperature.

EXAMPLE 3

Synthesis of S-Benzyl-S'-(11-undecanoic acid)trithiocarbonate (BUTTC)

A 500 ml three-necked round bottomed flask equipped with a mechanical paddle stirrer, nitrogen inlet, pot thermometer and condenser was charged under a slow nitrogen purge with 21.8 g (~0.10 moles) of 11-mercaptoundecanoic acid (I), 12.8 g (~0.20 moles) of 87.5 percent pure KOH and 100 ml of water. The mixture was stirred and warmed to 50° C. until all of (I) had dissolved and a clear solution was achieved. The solution was then cooled to ~30° C. before adding all at once a solution of 0.2 g of Aliquat 336 dissolved in 7.6 g (~0.10 moles) of carbon disulfide. An orange solution develops immediately and the solution temperature increases to ~45° C. within 10–15 min. After an additional 15 minutes, 12.02 g (~0.095 moles) of benzyl chloride. A slight temperature increase as the reaction proceeds and the mixture became very thick. After 10 min., an additional 100 ml of water was added to thin the mixture. After stirring an additional 10 min., the entire mixture was neutralized to an acidic pH with the addition of dilute hydrochloric acid. The bright yellow solid that forms was filtered off, washed with water followed by a hexane wash and then dried to give 39.26 g of crude product. The crude product was purified by dissolving it in 400 ml of water containing 4.5 g of sodium hydroxide followed by its reprecipitation using dilute HCl. NMR analysis indicates >95 percent purity of the desired structure.

COMPARATIVE EXAMPLE 4

The Controlled Anionic Emulsion Polymerization of Styrene Using BDTTC and Tripotassium Phosphate as Electrolyte A one liter three-necked round bottomed flask equipped with a mechanical paddle stirrer, nitrogen inlet, pot thermometer and condenser was charged with 2.55 g (~0.0069 moles) of BDTTC, 140 g (~1.34 moles) of styrene and 8.4 g (~0.0297 moles) of oleic acid. The mixture was stirred to form a homogeneous solution. In a separate flask, were dissolved 0.84 g (0.0031 moles) of potassium persulfate (KPS), 5.6 g (0.0264 moles) tripotassium phosphate, and 2.31 g (~0.0355 moles) of 87.5 percent pure of potassium hydroxide in 238 g of reverse osmosis (RO) treated water. The aqueous solution was then added to the stirred styrene solution all at once to rapidly generate a uniform emulsion. The system was then rapidly heated to 55° C. An exotherm carried the reaction temperature to ~78° C. before being cooled in a water bath to 75° C. Theoretical solids at 100 percent conversion are 40 percent. After 1 hour at 75° C. the solids were 39 percent. A small sample of the final latex was coagulated in dilute HCl, filtered, washed and dried for SEC analysis.

The Mn was determined to be 162,000 with a PDI of 1.85.

Theoretical Mn should be ~20,000.

These results indicate poor control over polymerization rate, MW and polydispersity by BDTTC in anionic emulsion polymerization.

EXAMPLE 4a

Synthesis of S-(4-Picolyl)-S'-(2-hydroxydecyl) trithiocarbonate (PHDTTC)

A 250 ml three-necked round bottomed flask equipped with a mechanical paddle stirrer, nitrogen inlet, pot thermometer and condenser was charged with 19.0 g (~0.10 moles) of 2-hydroxydecanethiol and 12.8 g (~0.20 moles) of potassium hydroxide dissolved in 50 ml of water under nitrogen with slow stirring. The thick clear mixture was stirred for 10 min. then cooled to room temperature before adding a solution of 0.25 g of Aliquat 336 dissolved in 15.2 (~0.20 moles) of carbon disulfide. The mixture rapidly turns bright yellow in color. Cool mixture to room temperature and stir for 10 min. Next, carefully add a solution of 4-picolyl hydrochloride dissolved in 20 ml water to the mixture. *Note: Heat of neutralization of hydrochloride salt with KOH may cause excessive foaming of excess carbon disulfide if temperature during addition is not carefully monitored. As the reaction proceeds, the lower product phase becomes brick red while the upper aqueous phase becomes a clear pale yellow. After 1.5 hours of stirring at room temperature, 50 ml of dichloromethane were added and the lower product phase separated. The solvent was then removed at reduced vacuum to give a dark red clear liquid, 34.2 g. This represents a crude yield of 95.5 percent.

COMPARATIVE EXAMPLE 5

The Controlled Anionic Emulsion Polymerization of Styrene Using BDTTC and Carbonate/Bicarbonate as Electrolyte A 500 ml three-necked round bottomed flask equipped with a mechanical paddle stirrer, nitrogen inlet, pot thermometer and condenser was charged with 5.67 g (~0.0153 moles) of BDTTC, 100 g (~0.96 moles) of styrene and 6.0 g (~0.0212 moles) of oleic acid. The mixture was stirred to form a homogeneous solution. In a separate flask, were dissolved 0.60 g (0.0022 moles) of potassium persulfate (KPS), 1.43 g (0.017 moles) sodium bicarbonate, 1.43 g (0.0135 moles) of sodium carbonate and 1.36 g (~0.021 moles) of 87.5 percent pure of potassium hydroxide in 185.6 g of reverse osmosis (RO) treated water. The aqueous solution was then added to the stirred styrene solution all at once to rapidly generate a uniform emulsion. The system was then rapidly heated to 55° C. An exotherm carried the reaction temperature to ~80° C. before being cooled in a water bath to 75° C. After 2 hours at 75° C. the solids were 35.7 percent. A small sample of the final latex was coagulated in dilute HCl, filtered, washed and dried for SEC analysis.

The Mn was determined to be 150,000 with a PDI of 1.26.

Theoretical Mn should be ~7000.

Once again, these results indicate poor control over polymerization rate, MW and polydispersity by BDTTC in anionic emulsion polymerization.

COMPARATIVE EXAMPLE 6

The Controlled Cationic Emulsion Polymerization of Styrene Using BDTTC

A 500 ml three-necked round bottomed flask equipped with a mechanical paddle stirrer, nitrogen inlet, pot thermometer and condenser was charged with 5.67 g (~0.0153 moles) of BDTTC, 100 g (~0.96 moles) of styrene and 5.23 g (~0.0176 moles) of octadecyldimethylamine. The mixture was stirred to form a homogeneous solution. In a separate flask, were dissolved 0.61 g (0.0022 moles) of potassium persulfate (KPS), 1.78 g (0.018 moles) of concentrated HCl in 178 g of reverse osmosis (RO) treated water. The aqueous solution was then added to the stirred styrene solution all at once to rapidly generate a uniform emulsion. The system was then heated to 65° C. Slight exotherm increased temperature to ~68° C. After 2.5 hrs., solids were 37.4 percent. A small sample of the final latex was coagulated in dilute HCl, filtered, washed and dried for SEC analysis.

The Mn was determined to be 178,000 with a PDI of 1.29.

Theoretical Mn should be ~7000.

Once again, these results indicate poor control over polymerization rate, MW and polydispersity by BDTTC in cationic emulsion polymerization.

EXAMPLE 7

The Controlled Anionic Emulsion Polymerization of Styrene Using BUTTC and Tripotassium Phosphate as Electrolyte A 500 ml three-necked round bottomed flask equipped with a mechanical paddle stirrer, nitrogen inlet, pot thermometer and condenser was charged with 6.38 g (~0.0153 moles) of BUTTC, 100 g (~0.96 moles) of styrene and 6.0 g (~0.0212 moles) of oleic acid. The mixture was stirred to form a homogeneous solution. In a separate flask, were dissolved 0.60 g (0.0022 moles) of potassium persulfate (KPS), 0.6 g (0.0028 moles) tripotassium phosphate and 2.34 g (~0.0365 moles) of 87.5 percent pure of potassium hydroxide in 170.0 g of reverse osmosis (RO) treated water. The aqueous solution was then added to the stirred styrene solution all at once to rapidly generate a uniform emulsion. The system was then heated to 70° C. After 6 hours at 70° C. the solids were 39.6 percent. A small sample of the final latex was coagulated in dilute HCl, filtered, washed and dried for SEC analysis.

The Mn was determined to be 35,400 with a PDI of 1.36.

Theoretical Mn should be ~7000.

These results represent a dramatic improvement over the use of BDTTC in comparative examples 4, 5 and 6. Polymerization rate is slower but much more easily controlled. MW is also much lower than when using BDTTC at the same molar level as in Comparative Example 5. Polydispersity is somewhat higher.

EXAMPLE 8

The Controlled Cationic Emulsion Polymerization of Styrene Using BHDTTC

A 500 ml three-necked round bottomed flask equipped with a mechanical paddle stirrer, nitrogen inlet, pot thermometer and condenser was charged with 5.95 g (~0.0153 moles) of BHDTTC, 100 g (~0.96 moles) of styrene and 5.23 g (~0.0176 moles) of octadecyldimethylamine. The mixture was stirred to form a homogeneous solution. In a separate flask, were dissolved 0.60 g (0.0022 moles) of potassium persulfate (KPS), 1.78 g (0.018 moles) of concentrated HCl in 178 g of reverse osmosis (RO) treated water. The aqueous solution was then added to the stirred styrene solution all at once to rapidly generate a uniform emulsion. The system was then heated to 70° C. After 11 hrs., solids were 36.5 percent (theory 38.3 percent). A small sample of the final latex was coagulated in dilute KOH, filtered, washed and dried for SEC analysis.

The Mn was determined to be 10,100 with a PDI of 1.27. Theoretical Mn should be ~7000.

These results represent an improvement over the use of BDTTC and BUTTC. Polymerization rate is slower but easily controlled.

EXAMPLE 9

The Controlled Cationic Emulsion Polymerization of Styrene Using BHDTTC

This reaction was run in an identical manner to Example 8 except that the level of BHDTTC was halved to 2.97 g (0.00765 moles). After 6 hrs., solids were 36.5 percent (theory 37.7 percent). A small sample of the final latex was coagulated in dilute KOH, filtered, washed and dried for SEC analysis.

The Mn was determined to be 19,700 with a PDI of 1.25. Theoretical Mn should be ~13,000.

EXAMPLE 10

The Controlled Cationic Emulsion Polymerization of Styrene Using BHDTTC

This reaction was run in an identical manner to Example 8 except that the level of BHDTTC was lowered to 1.48 g (0.0038 moles). After 4.5 hrs., solids were 37 percent (theory 37.4 percent). A small sample of the final latex was coagulated in dilute KOH, filtered, washed and dried for SEC analysis.

The Mn was determined to be 36,000 with a PDI of 1.30. Theoretical Mn should be ~26,000.

EXAMPLE 11

The Controlled Anionic Emulsion Polymerization of Styrene Using BHDTTC and Carbonate/Bicarbonate as Electrolyte A 500 ml three-necked round bottomed flask equipped with a mechanical paddle stirrer, nitrogen inlet, pot thermometer and condenser was charged with 2.97 g (~0.0076 moles) of BHDTTC, 100 g (~0.96 moles) of styrene and 6.0 g (~0.0212 moles) of oleic acid. The mixture was stirred to form a homogeneous solution. In a separate flask, were dissolved 0.60 g (0.0022 moles) of potassium persulfate (KPS), 1.37 g (0.0163 moles) sodium bicarbonate, 1.37 g (0.0129 moles) of sodium carbonate and 1.4 g (~0.0215 moles) of 87.5 percent pure of potassium hydroxide in 170 g of reverse osmosis (RO) treated water. The aqueous solution was then added to the stirred styrene solution all at once to rapidly generate a uniform emulsion. After 2 hours at 70° C. the solids were 37.9 percent. After 4 hours at 70° C., the polymerization was discontinued and filtered to remove ~10 g of granular yellow solid. A small sample of the final filtered latex was coagulated in dilute HCl, filtered, washed and dried for SEC analysis along with a sample of the granular yellow solid.

The Mn of the coagulated filtered latex sample was determined to be 31,700 with a PDI of 1.36 while the Mn of the granular solid was found to be 21,000 with a PDI of 1.21. Theoretical Mn should be ~13,000.

EXAMPLE 12

The Controlled Cationic Emulsion Polymerization of Styrene/Butadiene Using BHDTTC A 2 gallon reactor was initially flushed with nitrogen before being charged with a solution prepared from 540 g (5.19 moles) of styrene, 81.0 g (~0.27 moles) of N,N-dimethyloctadecylamine and 4.77 g (~0.0123 moles) of BHDTTC and stirred at 200 rpm. To this mixture was then added an aqueous solution prepared from 3510 g of RO water, 12.6 g (0.0466 moles) of potassium persulfate and 33.66 g of conc. Hydrochloric acid (~0.34 moles). The reactor was again flushed with nitrogen before adding 1260 g (~23.33 moles) of distilled butadiene. The stirred reactor was then heated to 65° C. with "solids" being taken every 2 hours to follow the progress of the polymerization. The reaction was shortstopped at ~23 percent solids (~65 percent conversion) with 45 g of a 2 percent aq. solution of 4-hydroxy TEMPO after 10.5 hours. The latex was then cooled and vacuumed stripped of residual monomers to yield a final latex with 24.1 percent solids, pH 1.53, viscosity of 352 cps, mechanical stability of 221 mg and an alcohol Mooney (ML4) of 37. NMR analysis indicates 23.3 percent styrene, 62.3 percent 1,4-BD and 14.4 percent 1,2-BD.

EXAMPLE 14

The Controlled Anionic Emulsion Polymerization of Styrene Using PHDTTC and Carbonate/Bicarbonate as Electrolyte A 500 ml three-necked round bottomed flask equipped with a mechanical paddle stirrer, nitrogen inlet, pot thermometer and condenser was charged with 2.74 g (~0.00765 moles) of PHDTTC, 100 g (~0.96 moles) of styrene and 6.0 g (~0.0212 moles) of oleic acid. The mixture was stirred to form a homogeneous solution. In a separate flask, were dissolved 0.60 g (0.0022 moles) of potassium persulfate (KPS), 1.2 g (0.0143 moles) sodium bicarbonate, 1.2 g (0.0113 moles) of sodium carbonate and 1.4 g (~0.0218 moles) of 87.5 percent pure of potassium hydroxide in 178 g of reverse osmosis (RO) treated water. The aqueous solution was then added to the stirred styrene solution all at once to rapidly generate a uniform emulsion. The mixture was then rapidly heated to 75° C. After 2.5 hrs, the latex solids were at 37.2 percent.

Theoretical Mn should be about 13,000. Mn against polystyrene standards by SEC was determined to be 29,400 with PDI of 1.08.

EXAMPLE 15

The Controlled Cationic Emulsion Polymerization of Styrene Using PHDTTC

A 500 ml three-necked round bottomed flask equipped with a mechanical paddle stirrer, nitrogen inlet, pot thermometer and condenser was charged with 2.74 g (~0.00765 moles) of PHDTTC, 100 g (~0.96 moles) of styrene and 5.23 g (~0.0176 moles) of octadecyldimethylamine. The mixture was stirred to form a homogeneous solution. In a separate flask, were dissolved 0.60 g (0.0022 moles) of potassium persulfate (KPS), 2.52 g (~0.0255 moles) of concentrated HCl in 178 g of reverse osmosis (RO) treated water. The aqueous solution was then added to the stirred styrene solution all at once to rapidly generate a uniform emulsion. The system was then heated to 75° C. After 3 hrs., solids were 36.2 percent (theory 37.6 percent). A small sample of the final latex was coagulated in dilute KOH, filtered, washed and dried for SEC analysis.

Theoretical Mn is about 13,000. SEC results show Mn of 147,000 with a PDI of 2.18 indicating that PHDTTC is a poor RAFT agent in an acidic cationic emulsion polymerization.

The following conclusions may be drawn from the foregoing examples:

(1) Surprisingly, the unsymmetrical trithiocarbonate CFR agents BHDTTC and BUTTC containing either a hydroxyl or carboxyl group respectively, perform exceptionally well in controlling molecular weight and polydispersity relative to their "unfunctionalized" counterpart (BDTTC) when using "in-situ" emulsion techniques.

(2) PHDTTC works well in anionic recipes but not acidic cationic ones.

(3) No instance could be found for the composition-of-matter for BHDTTC, BUTTC, or PHDTTC CFR agents or their use in combination with the "in-situ" emulsification technique.

(4) The processes for the preparation of BHDTTC, BUTTC and PHDTTC are simple, fast, high yielding, and solventless phase transfer catalyzed methods.

(5) Polymers prepared using either BHDTTC, BUTTC or PHDTTC prepared in bulk, solution or emulsion systems contain terminal functionality consisting of a trithiocarbonate group and either a hydroxyl, carboxyl or pyridyl group.

(6) Polymers from (4) above can function as macroinitiators for the subsequent formation of block, graft or gradient copolymers.

While certain representative embodiments and details have been shown for the purpose of illustrating the invention, it will be apparent to those skilled in this art that various changes and modifications may be made therein without departing from the spirit or scope of the invention.

What is claimed is:

1. A free radical control agent of the structural formula:

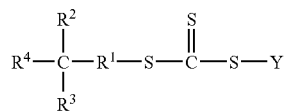

wherein $R^1$ is a divalent alkyl group of 1 to 12 carbon atoms, $R^2$ and $R^3$ are each independently hydrogen or an alkyl group of 1 to 12 carbon atoms, and $R^4$ is —OH or —COOH, with the proviso that the total carbon atoms of $R^1$, $R^2$, and $R^3$ is no greater than 12; and wherein Y represents a functional group that is capable of activating a vinylic carbon toward free radical addition.

2. A free radical control agent according to claim 1 wherein Y represents a functional group selected from the group consisting of —C(R')$_2$CN, —C(CH$_3$)$_2$Ar, —C(CH$_3$)$_2$COOR', —C(CH$_3$)$_2$CONHR', —C(CH$_3$)$_2$CH$_2$C(CH$_3$), —CH(CH$_3$)Ar, —CH$_2$Ar, —C(CH$_3$)$_3$, —CR'$_2$COOH, —C(R')(CN)—(CH$_2$)$_n$—COOH, and —C(R')(CN)—(CH$_2$)$_n$—OH; wherein R' represents a linear or branched hydrocarbon containing from 1 to 12 carbon atoms; wherein Ar represents an unsubstituted or substituted phenyl, napthyl, anthracenyl, pyrenyl or pyridyl group; and wherein n represents an integer from 1 to 8.

3. A free radical control agent according to claim 1 wherein $R^1$ is (CH$_2$)$_m$ where m ranges from 1 to 4.

4. A free radical control agent according to claim 1 wherein Y represents a function group selected from the group consisting of benzyl, picolyl, and t-butyl.

5. A free radical control agent according to claim 1, wherein $R^1$ is (CH$_2$)$_9$, $R^2$ and $R^3$ are hydrogen, $R^4$ is —COOH, Y is benzyl, and the free radical control agent is S-benzyl-S'-(11-undecanoic acid)trithiocarbonate.

6. A free radical control agent according to claim 1, wherein $R^1$ is CH$_2$, $R^2$ is (CH$_2$)$_8$, $R^3$ is hydrogen, $R^4$ is —OH, Y is benzyl, and the free radical control agent is S-benzyl-S'-(2-hydroxydecyl)trithiocarbonate.

7. A free radical control agent according to claim 1, wherein $R^1$ is CH$_2$, $R^2$ is (CH$_2$)$_8$, $R^3$ is hydrogen, $R^4$ is —OH, Y is 4-picolyl, and the free radical control agent is S-(4-Picolyl)-S'-(2-hydroxydecyl)trithiocarbonate.

8. A polymer derived from the free radical control agent of claim 1 and at least one monomer selected from the group consisting of styrene, substituted styrene, alkyl acrylate, substituted alkyl acrylate, alkyl methacrylate, substituted alkyl methacrylate, acrylonitrile, methacrylonitrile, acrylamide, methacrylamide, N-alkylacrylamide, N-alkylmethacrylamide, N,N-dialkylacrylamide, N,N-dialkylmethacrylamide, isoprene, 1,3-butadiene, ethylene, vinyl acetate, vinyl chloride, and vinylidene chloride.

9. A polymer derived from the free radical control agent of claim 1 and at least one monomer selected from the group consisting of styrene, 1,3-butadiene, and isoprene.

10. A tire comprising the polymer of claim 8.

* * * * *